United States Patent
Meredith

(10) Patent No.: US 7,001,551 B2
(45) Date of Patent: *Feb. 21, 2006

(54) METHOD OF FORMING A COMPOSITE BONE MATERIAL IMPLANT

(75) Inventor: Thomas L. Meredith, Nashville, TN (US)

(73) Assignee: Allograft Research Technologies, Inc., Nashville, TN (US)

( * ) Notice: Subject to any disclaimer, the term of this patent is extended or adjusted under 35 U.S.C. 154(b) by 402 days.

This patent is subject to a terminal disclaimer.

(21) Appl. No.: 10/128,219

(22) Filed: Apr. 23, 2002

(65) Prior Publication Data

US 2003/0036800 A1 Feb. 20, 2003

Related U.S. Application Data

(63) Continuation-in-part of application No. 09/615,643, filed on Jul. 13, 2000, now abandoned.

(51) Int. Cl.
*B29C 43/56* (2006.01)
*B29C 43/02* (2006.01)
*A61F 2/28* (2006.01)
*A61F 2/30* (2006.01)

(52) U.S. Cl. .............. 264/101; 264/553; 264/571; 264/109; 264/115; 264/128; 264/162; 264/319; 264/328.1; 264/87; 264/DIG. 78; 623/23.63

(58) Field of Classification Search .............. 264/553, 264/571, 101, 109, 115, 128, 162, 319, 328.1, 264/DIG. 78, 87; 623/23.63
See application file for complete search history.

(56) References Cited

U.S. PATENT DOCUMENTS

| 3,825,640 | A | * | 7/1974 | Maierson | 264/87 |
| 3,852,045 | A | | 12/1974 | Wheeler et al. | 29/182 |
| 3,975,479 | A | * | 8/1976 | McClean | 264/102 |
| 4,522,753 | A | * | 6/1985 | Yannas et al. | 530/356 |
| 4,645,503 | A | | 2/1987 | Lin et al. | 2/28 |
| 4,678,470 | A | | 7/1987 | Nashef et al. | |
| 4,843,112 | A | | 6/1989 | Gerhart et al. | 3/32 |
| 4,947,840 | A | * | 8/1990 | Yannas et al. | 602/50 |
| 5,061,286 | A | | 10/1991 | Lyle | 2/28 |
| 5,439,684 | A | | 8/1995 | Prewett et al. | 17/56 |
| 5,501,706 | A | * | 3/1996 | Arenberg | 623/23.56 |
| 5,507,813 | A | | 4/1996 | Dowd et al. | 2/28 |
| 5,516,532 | A | | 5/1996 | Atala et al. | 35/32 |
| 5,545,222 | A | | 8/1996 | Bonutti | 2/2 |
| 5,565,502 | A | | 10/1996 | Glimcher et al. | 3/32 |

(Continued)

OTHER PUBLICATIONS

U.S. Appl. No. 09/615,643, filed Jul. 13, 2000, Meredith.

*Primary Examiner*—Michael P. Colaianni
*Assistant Examiner*—Michael I. Poe
(74) *Attorney, Agent, or Firm*—Waddey and Patterson, P.C.; Phillip E. Walker

(57) ABSTRACT

A method of forming a bone composite, comprising: providing bone tissue; grinding said bone tissue to form ground tissue; molding the ground bone tissue into a bone composite; applying a binder to the bone composite; applying a vacuum to the mold, and optionally milling or refining the bone composite to the desired shape. Additionally, bone tissue composites made therefrom are included. The composites may be, for example, a bone pin, screw, or prosthesis.

42 Claims, 4 Drawing Sheets

U.S. PATENT DOCUMENTS

| | | |
|---|---|---|
| 5,658,334 A | 8/1997 | Caldarise et al. .............. 623/16 |
| 5,662,710 A | 9/1997 | Bonutti ............................. 2/2 |
| 5,824,078 A | 10/1998 | Nelson et al. |
| 5,899,939 A | 5/1999 | Boyce et al. ..................... 2/28 |
| 6,025,538 A | 2/2000 | Yaccarino, III ................... 2/28 |
| 6,045,554 A | 4/2000 | Grooms et al. ................. 17/86 |
| 6,090,998 A | 7/2000 | Grooms et al. ................... 2/28 |
| 6,123,731 A * | 9/2000 | Boyce et al. ............. 623/23.63 |
| 6,132,472 A | 10/2000 | Bonutti ............................. 2/2 |
| 6,136,029 A | 10/2000 | Johnson et al. ................... 2/28 |
| 6,187,329 B1 | 2/2001 | Agrawal et al. .................... 2/2 |
| 6,210,031 B1 | 4/2001 | Murray ............................. 13/6 |
| 6,294,187 B1 | 9/2001 | Boyce et al. |
| 6,521,284 B1 * | 2/2003 | Parsons et al. ............. 427/2.24 |
| 2003/0083752 A1 * | 5/2003 | Wolfinbarger et al. ... 623/23.63 |
| 2003/0217415 A1 * | 11/2003 | Crouch et al. ............... 8/94.11 |

\* cited by examiner

METHOD OF FORMING A COMPOSITE BONE MATERIAL IMPLANT

This patent application is a continuation-in-part of U.S. patent application Ser. No. 09/615,643, filed Jul. 13, 2000 now abandoned, the contents of which are expressly incorporated herein by reference.

FIELD OF THE INVENTION

This invention generally relates to the field of bone composite implants and a method of forming bone composites. The bone composite implants, or osteoimplants, of the present invention may be used in the repair, replacement, and/or augmentation of various portions of animal or human skeletal systems. The bone composite implants of the present invention may be considered load-bearing implants.

The composite of the present invention is generally formed from a process comprising grinding bone tissue to form ground tissue, molding the ground bone tissue at least under vacuum into a bone composite, and optionally applying a binder to the bone composite.

BACKGROUND OF THE INVENTION

The practice of donating and transplanting bone tissue is beginning to form an important part of therapy for a number of ailments involving bone.

FIG. 1 is a three-dimensional diagram showing the appearance of both a cross and a longitudinal section of an example of a bone structure, and shows various components of the bone. Of course, FIG. 1 is not as detailed as possible, and does not feature every element of bone tissue. The purpose of FIG. 1 is only to briefly show some features of natural bone which also occur in the bone composites of the present invention. With respect to FIG. 1, a bone 10 section is shown. Lamellae 15 are shown within the bone cross section. The haversian canals 20 are shown. In the longitudinal section of the drawing, blood vessels 25 are shown in connection with the haversian canals 20. Finally, the marrow portion 30 is shown with blood vessels 25 extending into the marrow portion of the bone.

Tissue grafting of living tissue from the same patient, including bone grafting, is well known in medical science. Tissue such as bone is removed from one part of a body (the donor site) and inserted into tissue in another (the host site) part of the same (or another) body. This method has been desirable in the past because the tissue was believed to be highly osteoconductive. With respect to living bone tissue, it has been desirable in the past to be able to remove a piece of living tissue graft material which is the exact size and shape needed for the host site where it will be implanted, but it has often proved very difficult to achieve this goal.

Until recently, developers of bone transplants and prostheses have believed that it is desirable to maintain graft tissue in a living state during the grafting process. It is relatively undisputed that the use of living tissue in a graft will promote bone healing, but recent surgical experience has shown that healing can be achieved with allografts of non-living bone material which has been processed.

Processing of bone material which does not contain living tissue is becoming more and more important. Non-living bone grafting techniques have been attempted both for autografts and for allografts. The use of autograft bone is where the patient provides the source of the bone, and the use of allograft bone is where another individual of the same species provides the source of the bone.

In the prior art, transplanted bone has been used in the past to provide support, promote healing, fill bony cavities, separate bony elements (such as vertebral bodies), promote fussion (where bones are induced to grow together in a single, solid mass), or stabilize the sites of fractures.

For example, Nashef U.S. Pat. No. 4,678,470 discloses a method of creating bone graft material by machining a block of bone to a particular shape or by pulverizing and milling it. The graft material is then tanned with glutaraldehyde to sterilize it. This process can produce bone plugs of a desired shape.

In the Nashef process, the process of pulverizing or milling the bone material destroys the structure of the bone tissue. The step of tanning it with glutaraldehyde then renders the graft material completely sterile.

It is now possible to obtain allograft bone which has been processed to remove all living material which could present a tissue rejection problem or an infection problem. Such processed material retains much of the mineral quality of the original living bone, rendering it more osteoinductive. Moreover, it can be shaped according to known and new methods to attain enhanced structural behavior. In fact spine surgeons express a distinct preference for such materials, and at least one supplier, the Musculoskeletal Transplant Foundation (MTF), has introduced femoral ring allografts for spine surgeries.

Research shows that such allografts are very favorable for spinal surgery. According to Brantigan, J. W., Cunningham, B. W., Warden, K., McAfee, P. C., and Steffee, A. D., A compression Strength of Donor Bone for Posterior Lumbar Interbody Fusion, *Spine*, Vol. 18, No. 9, pp. 12113–21 (July 1993):

Many authors have viewed donor bone as the equivalent of autologous bone. Nasca, et al . . . compared spinal fusions in 62 patients with autologous bone and 90 patients with cryopreserved bone and found successful arthrodesis in 87% of autologous and 86.6% of allograft patients. (Citations omitted.).

A drawback of fabricating transplants and prostheses from donated allograft is that the process necessitates discard of a great deal of scrap and powdered bone material. Good quality donated bone is a scarce resource, so that devising a method of using scrap and powdered allograft bone material would be of great assistance to this highly beneficial endeavor. The present invention uses ground bone to make solid shapes. The results of the present invention are superior to the prior art processes and the process and composite of the present invention allows for a greater amount of donor bone to become available. For example, with the present invention, bone can now be used from older donors. With a transplanted allograft, older bone may be too brittle and weak.

In the fabrication of bone transplants, it was observed that bone material which yields to compressive loads at the exterior surfaces without significant degradation of the interior structural properties, such as cancellous or trabecular bone, can be shaped. It is not unusual that reshaping of a graft tissue is necessary to obtain the best possible graft. In particular, bone tissue may be stronger and better able to bear force when it is denser and more compact.

Additionally, prior art techniques have a serious limitation in that bone parts and bone products made from allograft cortical tissue may be limited in size, dimension and shape because of the anatomical limits on the thickness and length of the source bone. With the method of the present invention, many shapes and forms can be fabricated from allograft cortical bone tissue including pins, screws, plates, intervertebral discs, and the like for use in surgery.

Allograft bone occurs in two basic forms: cancellous bone (also referred to as trabecular bone) and cortical bone. Cortical bone is highly dense and has a compound structure comprised of calcium hydroxyapatite reinforced with collagen fiber. In the present invention, cortical bone tissue is preferred.

Compression of allograft bone is desirable from general considerations. Generally, bone samples are stronger when they are more dense. Compressing allograft bone increases its density and thus generally strengthens the allograft. In addition, recent studies have indicated that the shell of vertebral bone is very much like condensed trabecular bone. Mosekilde, L., A Vertebral structure and strength in vivo and in vitro, Calc. Tissue Int. 1993;53 (Suppl):121–6; Silva, M. J., Wang, C., Keaveny, T. M., and Hayes, W. C., A Direct and computed tomography thickness measurements of the human lumbar vertebral shell and endplate, Bone 1994:15: 409–14; Vesterby, A., Mosekilde, L., Gunderson, H. J. G., et al., Biologically meaningful determinants of the in vitro strength of lumbar vertebrae, Bone 1991;12:219–24.

Compression also allows conversion of larger irregular shapes into the desirable smaller shape, thereby permitting more disparate sources of allograft bone to be used. By compressing bone to a given shape it is possible to configure the allograft to match a preformed donee site prepared by using a shaped cutter to cut a precisely matching cut space. In particular, this method of formation facilitates the formation of match mated surfaces of the implant for the formation of a particular shape for skeletal repair or revision.

For the reasons stated above, in certain embodiments of the present invention, compression is useful as part of the molding step in forming the bone composites of the present invention. However, an advantage of the present invention is that in some embodiments compression is not required, and in some embodiments it is preferred—but at very low pressure when compared to the compression levels of the prior art.

It is known that allograft bone can be reshaped into one of many configurations for use as an implant. Various methods, including that of Bonutti, U.S. Pat. Nos. 5,662,710 and 5,545,222, can be used to shape allograft material into the desired shape.

A goal of a bone composite transplant is that the transplant is readily received and hosted by the receiving mammal, with bone fusion occuring (i.e., the composite should be biocompatible and osteoinductive). Today, the only other osteoinductive implants are allograft shapes that have been cut and shaped from cadaver donated bone. This method has serious drawbacks in that it is difficult for sufficient fusion to take place and the implant usually lacks sufficient structural strength and density.

U.S. Pat. No. 6,025,538 to Yaccarino, III, discloses allograft bone devices for surgical implantation in the bone tissue.

U.S. Pat. No. 5,439,864 to Pruitt, et al., discloses shaped demineralized bone for use in the surgical repair of bone defects.

U.S. Pat. No. 5,662,710 to Bonutti, discloses a tissue press for shaping or compressing a piece of graft tissue.

U.S. Pat. No. 5,899,939 to Boyce et al. discloses a bone-derived implant that comprises cortical bone and is used to repair, replace, or augment various portions of animal and human skeletal systems. The bone implant of this invention is made up as individual layers that may be held together by adhesives. Finally, the bone-derived implant of this invention may have one or more cavities which may be filed with demineralized bone powder. This patent fails to disclose making an implant or prosthesis from ground bone powder.

U.S. Pat. No. 6,025,538 to Yaccarino, III discloses allograft bone devices for surgical implantation in the bone tissue. The device is larger than the natural dimensions of a cortical bone layer and is made by combining two or more smaller pieces to form a compound bone structure. A pin may be placed through the component bone members of the bone structure. Finally, each bone member is shaped to form a groove to receive the end of the other bone member. The device of this invention may be processed to form compound bone pins, bone screws, plates, disks, wedges, blocks, etc. The devices may be secured together by using any surgical bone adhesive with a synthetic absorbable or nonabsorbable polymer in connection with the pin that connects the two bone pieces together.

U.S. Pat. No. 6,090,998 to Grooms et al. discloses a unitary bone implant having at least one rigid, mineralized bone segment. The implant may be machined to include threads, grooves, etc. to provide a means for fixation of the implant directly to a bone machined in a complimentary fashion. The implant of this invention may be used to repair or replace ligaments, tendons, and joints.

U.S. Pat. No. 6,045,554 to Grooms et al. discloses an interference screw manufactured from cortical allograft bone tissue may be used as a fixation screw for cruciate ligament graphs. The screw is made by obtaining a fragment of bone from the cortex and machining the thread, tip and drive head of the screw. More specifically, the section is removed from a femur or tibia, a dowel of the tissue is machined. The machining may be done by a grinding wheel.

U.S. Pat. No. 5,507,813 to Dowd et al. discloses a process for making surgically implantable materials fabricated from elongate bone particles. The particles may be graded into different sizes. Additionally, the particles are described as filaments, fibers, threads, slender or narrow strips, etc. The elongate bone particles may be mixed with an adhesive and/or filler. The fillers include bone powder.

U.S. Pat. No. 5,061,286 to Lyle discloses an osteoprosthetic implant with demineralized bone powder attached thereto. The bone powder apparently provides an osteogenic coating for the prosthesis. This coating allows the prosthesis to be firmly anchored to the bone repair site. The prosthesis device may be polymeric. The bone particles may be adhere to the prosthetic device and each other by a binder. Cyanoacrylate is disclosed as one of the binders.

U.S. Pat. No. 5,516,532 to Atala et al. discloses a method of making a cartilage and bone preparation using ground bone. The ground bone is apparently mixed with polymeric carriers and provides a suspension that may be injectable and used for correction of a variety of tissue defects. The suspension is typically injected through a cystoscopic needle or via a syringe directly into a specific area where the bulking is required.

U.S. Pat. No. 6,136,029 to Johnson et al. discloses an open-celled article that is useful as a bone substitute material that is highly porous and is of low density. The article comprises a framework that is preferably ceramic.

U.S. Pat. No. 6,294,187 to Boyce, et al. discloses an osteoimplant for use in the repair, replacement, and/or augmentation of various portions of animal or human skeletal systems. The implant of this patent comprises bone particles in combination with one or more biocompatible components. The implant is made by applying compressive force of at least 1,000 psi to the composition.

U.S. Pat. No. 5,565,502 to Glimcher, et al. discloses a process for removing and isolating the calcium-phosphate crystals of bone. The bone powder is prepared by milling bone in liquid nitrogen and sieving to a particle size ranging up to approximately 20 microns. The bone particles are then suspended in an organic solvent. The purified calcium-phosphate crystals are isolated from the bone and are useful as an aid to induce and promote bone healing.

U.S. Pat. No. 5,824,078 to Nelson, et al. discloses an allograft bone press. The bone press is used to compress cancellous bone chips to conform to a shape of a mold.

U.S. Pat. No. 4,645,503 to Lin, et al. discloses moldable bone-implant material. This material is prepared by mixing hard bone-graft filler particles with a biocompatible thermoplastic binder.

U.S. Pat. No. 4,843,112 to Gerhart, et al. discloses a moldable, biocompatible, polyester-particulate composite that can be used for reinforcement of fractures in a bone. This invention is directed to a biodegradable cement composition adapted for use in the surgical repair of living bone and for the controlled-released delivery of pharmaceutical agents.

U.S. Pat. No. 6,132,472 to Bonutti discloses a tissue press for shaping or compressing a piece of tissue. This apparatus and method is designed to press or shape tissue while preserving the tissue alive.

In response to the need for a composite material to make use of bone fragments and bone powder for fabricating implants and prosthetic devices for bone the current inventor developed the present invention.

SUMMARY OF THE INVENTION

An object of the present invention is to produce a bone tissue composite that is osteoinductive and has excellent strength characteristics, including excellent load-bearing ability.

Another object of the current invention is to provide a composite material utilizing bone powder and/or fragments as well as a method to manufacture and shape the composite into usable implants and/or bone prostheses. In preferred embodiments of the present invention, composite formed from the method of the present invention is of sufficient strength in a body fluid environment to enable the osteoimplant to bear loads.

Another object of the present invention is to provide a method which enables the fabrication of the composites into any size or shape for use as an implant.

Furthermore, it is an object of the present invention to provide a bone composite that is readily received and hosted when received by another mammal. The composite of the present invention allows bone fusion to occur, and the biocompatible and osteoinductive process allows the body to lay down native bone in combination with the implanted bone composite.

More specifically, the present invention relates to a method of forming a bone composite, comprising: providing bone tissue; grinding said bone tissue to form ground tissue; transferring the ground bone tissue into a mold; applying a binder to the bone tissue; applying a vacuum to the mold; and optionally milling or refining the bone composite to the desired shape. Preferably, the bone tissue is substantially cortical bone tissue (i.e., greater than about 40–50%), and preferably, the bone tissue is substantially demineralized (i.e., greater than about 40–50%).

More preferably, the bone tissue is greater than about 50% cortical bone tissue, more preferably in the range of greater than about 50–70% cortical bone tissue, more preferably in the range of greater than about 50–90% cortical bone tissue, more preferably in the range of greater than about 50–95% cortical bone tissue, more preferably 90% cortical bone tissue, and more preferably greater than about 95% cortical bone tissue. The size of the ground bone particles can vary, but typically the particles will range in size from 125 to 850 microns in size.

The molding process of the present invention occurs at from 14.7 psi (atmospheric pressure) to less than about 1,000 psi. Preferably, the above-mentioned occurs at below than 500 psi. Most preferably, the above-mentioned occurs at below about 200 psi.

Another embodiment of the present invention is a method of forming a bone composite, comprising: (i) providing bone tissue; (ii) grinding said bone tissue to form ground bone tissue ranging in size from about 125 microns to about 850 microns; (iii) transferring said ground bone tissue into a mold; (iv) applying a cyanoacrylate binder to the bone tissue; (v) applying a vacuum to the mold; (vi) applying a compressive force of less than 1000 psi to the mold; and (vii) optionally milling or refining the bone composite to the desired shape.

Another embodiment is a bone composite produced by one of the processes of the present invention. This composite is osteoinductive, and comprises ground bone tissue molded to form a desired shape, and a cyanoacrylate binder. The molded bone composite of the present invention further comprises random voids. The voids, discussed further below, aid osteoconductivity.

These and other embodiments will become apparent in the more detailed disclosure that follows.

BRIEF DESCRIPTION OF THE DRAWINGS

FIG. 1 shows a few of the features that appear in natural bone.

DETAILED DESCRIPTION OF THE PREFERRED EMBODIMENTS

Figure 1:
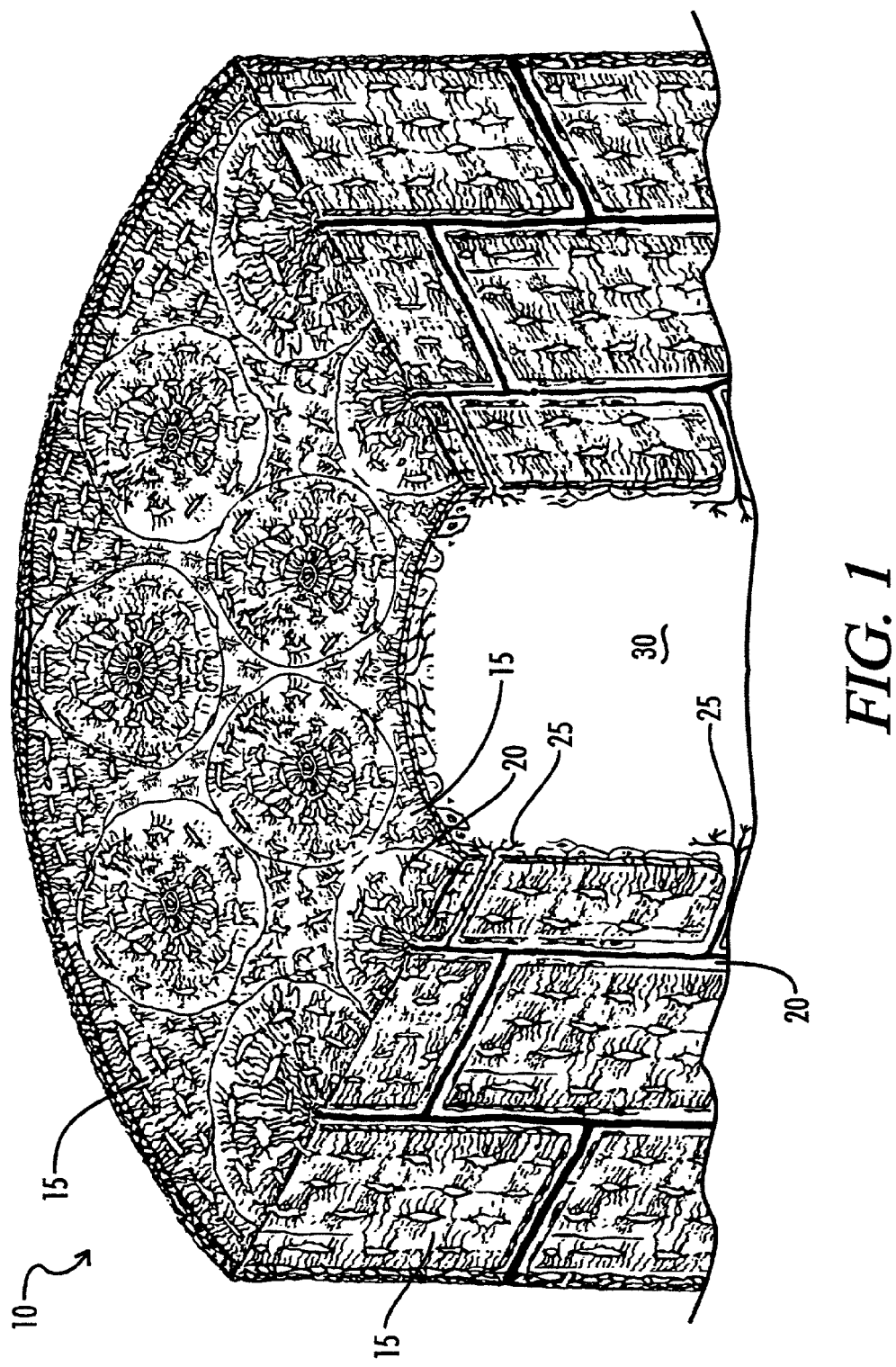
FIG. 1 shows a 3-dimensional diagram of a cross and longitudinal section of a bone portion.

The method and composite of the present invention can be used with any mammal, preferably horses and humans, most preferably humans. However, it is preferred that donor bone is the same species as recipient bone. That is, preferably human bone is used in making a bone composite that will be used by a human. Preferably the bone tissue is demineralized.

"Demineralized," as applied to the bone particles used herein, is intended to cover all bone particles that have had some portion of their original mineral content removed by a demineralization process. The bone particles are optionally demineralized in accordance with known and conventional procedures in order to reduce their inorganic mineral content. Demineralization methods remove the inorganic mineral component of bone by employing acid solutions. Such methods are well known in the art, see for example, Reddi et al., Proc. Nat. Acad. Sci. 69, pp 1601–1605 (1972). The strength of the acid solution, the shape of the bone particles and the duration of the demineralization treatment will determine the extent of demineralization. Reference in this regard may be made to Lewandrowski et al., J Biomed Materials Res, 31, pp 365–372 (1996). Additionally, the bone particles may be demineralized as set forth in U.S. Pat. No. 6,294,187.

As utilized herein, the phrase "superficially demineralized" as applied to the bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, preferably less than about 1, weight percent of their original inorganic mineral content. The unmodified term "demineralized" as applied to the bone particles is intended to cover any one or combination of the foregoing types of demineralized bone particles.

The type of mammalian bone that is most plentiful and most preferred as a resource for the composites of the present invention is cortical bone, which is also the form of bone tissue with the greatest compressive strength. As stated above, preferably cortical bone tissue is used to form the composites of the present invention. Also, preferably, the composites are substantially cortical bone tissue. As another preferred embodiment, the composites are above 50% cortical bone tissue, more preferably the bone tissue is greater than about 70%, greater than about 90%, or greater than about 95% cortical bone tissue.

The bone tissue is ground or pulverized. Pulverized bone can be collected and separated into a number of batches, each batch comprising a different mean particle size. The particle size can vary from fine to coarse. The properties of the composite to be produced can be tailored by choice of particle size. For example, particles in the range of from about 125 to about 850 microns can be used for making bone composites useful for skeletal repair and revision.

The resulting bone powder is placed in a mold and compressed using compression tooling. The measurements of the bone powder (weights and volume) are all predetermined, and one of ordinary skill in the art would understand the measurements to be dependant upon the size and shape of the desired resulting composite to be manufactured.

In a preferred embodiment, the ground bone tissue is hydrated before being place in the mold. Most preferably, the ground bone tissue is hydrated in an amount of about 1 to about 10% (volume), preferably in an amount of about 1 to about 5%. The hydrate is preferably dimineralized water, and is preferably applied by injection, spray bath, or soaking.

The mold may be any commercially mold that has pneumatic or vacuum capabilities. Preferably, the mold is a virgin Teflon®, or polyethylene mold that is contained in a stainless steel envelope. The mold preferably has a stainless steel pneumatic cylinder, vacuum pump, exhaust filtration, and pneumatic silencers.

Typically the input pressure, bore size of the pneumatic cylinder, and vacuum level (inches of Hg based on a standard barometer reading at atmospheric pressure (14.7 psi)) is predetermined and dependent upon the desired size, desired shape, and desired density of the composite to be manufactured. For example, We need at least the following: Input pressure; bore size of the pneumatic cylinder; vacuum level during CA fill, etc.

The mold preferably will incorporate predetermined number of orifices of a predetermined size, to help assure that the composite will receive evenly distributed pneumatic induced pressure and vacuum flow (Pascal's law).

The bone particles of the present invention may be combined with one or more of the biocompatible components set forth in U.S. Pat. No. 6,294,187, incorporated herein by reference. That is, the present invention may be combined with one or more biocompatible components such as wetting agents, biocompatible binders, fillers, fibers, plasticizers, biostatic/biocidal agents, surface active agents, bioactive agents, and the like, prior to, during, or after compressing the bone particle-containing composition. One or more of such components can be combined with the bone particles by any suitable means, e.g., by soaking or immersing the bone particles in a solution or dispersion of the desired component, by physically admixing the bone particles and the desired component, and the like.

At least a binder is applied to the bone powder. The binder may be applied by an injection, spray, bath, soaking, or layering. Preferably the binder is applied to the bone tissue in the mold, and preferably during a period while the mold is under vacuum. The binder should be biocompatible. Preferably the binder is a cyanoacrylate.

Suitable wetting agents include biocompatible liquids such as water, organic protic solvent, aqueous solution such as physiological saline, concentrated saline solutions, sugar solutions, ionic solutions of any kind, and liquid polyhydroxy compounds such as glycerol and glycerol esters, and mixtures thereof. The use of wetting agents in general is preferred in the practice of the present invention, as they improve handling of bone particles. When employed, wetting agents will typically represent from about 20 to about 80 weight percent of the bone particle-containing composition, calculated prior to compression of the composition. Certain wetting agents such as water can be advantageously removed from the osteoimplant, e.g., by heating and lyophilizing the osteoimplant.

Suitable biocompatible binders include biological adhesives such as fibrin glue, fibrinogen, thrombin, mussel adhesive protein, silk, elastin, collagen, casein, gelatin, albumin, keratin, chitin or chitosan; cyanoacrylates; epoxy-based compounds; dental resin sealants; bioactive glass ceramics (such as apatite-wollastonite), dental resin cements; glass ionomer cements (such as Lonocap® and Inocem® available from Ionos Medizinische Produkte GmbH, Greisberg, Germany); gelatin-resorcinol-formaldehyde glues; collagen-based glues; cellulosics such as ethyl cellulose; bioabsorbable polymers such as starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, poly (propylene glycol-co-fumaric acid), tyrosine-based polycarbonates, pharmaceutical tablet binders (such as Eudragit® binders available from Huls America, Inc.), polyvinylpyrrolidone, cellulose, ethyl cellulose, micro-crystalline cellulose and blends thereof; starch ethylenevinyl alcohols, polycyanoacrylates; polyphosphazenes; nonbioabsorbable polymers such as polyacrylate, polymethyl methacrylate, polytetrafluoroethylene, polyurethane and polyamide; etc. Preferred binders are polyhydroxybutyrate, polyhydroxyvalerate and tyrosine-based polycarbonates. When employed, binders will typically represent from about 5 to about 70 weight percent of the bone particle-containing composition, calculated prior to compression of the composition.

The binder acts as a matrix which binds the bone particles, thus providing coherency in a fluid environment and also improving the mechanical strength of the osteoimplant. Preferably, the binder is a cyanoacrylate binder. More preferably, the cyanoacrylate binder comprises ester chain, N-butyl, or butyl cyanoacrylates. Also, preferably the cyanoacrylate is a long chain cyanoacrylates.

Suitable fillers include graphite, pyrolytic carbon, bioceramics, bone powder, demineralized bone powder, anorganic bone (i.e., bone mineral only, with the organic constituents removed), dentin tooth enamel, aragonite, calcite, nacre, amorphous calcium phosphate, hydroxyapatite, tricalcium phosphate, Bioglass® and other calcium phosphate materials, calcium salts, etc. Preferred fillers are demineralized bone powder and hydroxyapatite. When employed, filler will typically represent from about 5 to about 80 weight percent of the bone particle-containing composition, calculated prior to compression of the composition.

Suitable fibers include carbon fibers, collagen fibers, tendon or ligament derived fibers, keratin, cellulose, hydroxyapatite and other calcium phosphate fibers. When employed, fiber will typically represent from about 5 to about 75 weight percent of the bone particle-containing composition, calculated prior to compression of the composition.

Suitable plasticizers include liquid polyhydroxy compounds such as glycerol, monoacetin, diacetin, etc. Glycerol and aqueous solutions of glycerol are preferred. When employed, plasticizer will typically represent from about 20 to about 80 weight percent of the bone particle-containing composition, calculated prior to compression of the composition.

Suitable biostatic/biocidal agents include antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, povidone, sugars, mucopolysaccharides, etc. Preferred biostatic/biocidal agents are antibiotics. When employed, biostatic/biocidal agent will typically represent from about 10 to about 95 weight percent of the bone particle-containing composition, calculated prior to compression of the composition.

Suitable surface active agents include the biocompatible nonionic, cationic, anionic and amphoteric surfactants. Preferred surface active agents are the nonionic surfactants. When employed, surface active agent will typically represent from about 1 to about 80 weight percent of the bone particle-containing composition, calculated prior to compression of the composition.

Any of a variety of bioactive substances can be incorporated in, or associated with, the bone particles. Thus, one or more bioactive substances can be combined with the bone particles by soaking or immersing the bone particles in a solution or dispersion of the desired bioactive substance(s). Bioactive substances include physiologically or pharmacologically active substances that act locally or systemically in the host.

Bioactive substances which can be readily combined with the bone particles include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digesters; antitumor agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. Preferred bioactive substances are currently bone morphogenic proteins and DNA delivered by plasmid or viral vector. When employed, bioactive substance will typically represent from about 0.1 to about 20 weight percent of the bone particle-containing composition, calculated prior to compression of the composition.

It will be understood by those skilled in the art that the foregoing biocompatible components are not intended to be exhaustive and that other biocompatible components may be admixed with bone particles within the practice of the present invention.

The total amount of such optionally added biocompatible substances will typically range from about 0 to about 95% weight/volume (w/v), preferably from about 1 to about 60% w/v, more preferably from about 5 to about 50% w/v, weight percent of the bone particle-containing composition, based on the weight of the entire composition prior to compression of the composition, with optimum levels being readily determined in a specific case by routine experimentation.

One method of fabricating the bone particle-containing composition which can be advantageously utilized herein involves wetting a quantity of bone particles, of which at least about 60 weight percent preferably constitute elongate bone particles, with a wetting agent as described above to form a composition having the consistency of a slurry or paste. Optionally, the wetting agent can comprise dissolved or admixed therein one or more biocompatible substances such as biocompatible binders, fillers, plasticizers, biostatic/biocidal agents, surface active agents, bioactive substances, etc., as previously described.

Preferred wetting agents for forming the slurry or paste of bone particles include water, liquid polyhydroxy compounds and their esters, and polyhydroxy compounds in combination with water and/or surface active agents, e.g., the Pluronics® series of nonionic surfactants. Water is the most preferred wetting agent for utilization herein. The preferred polyhydroxy compounds possess up to about 12 carbon atoms and, where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it improves the handling characteristics of the bone particles wetted therewith and is biocompatible and easily metabolized. Mixtures of polyhydroxy compounds or esters, e.g., sorbitol dissolved in glycerol, glycerol combined with monoacetin and/or diacetin, etc., are also useful. Where elongate bone particles are employed, some entanglement of the wet bone particles will result. Preferably, excess liquid can be removed from the slurry or paste, e.g., by applying the slurry or paste to a form such as a flat sheet, mesh screen or three-dimensional mold and draining away excess liquid.

Where, in a particular composition, the bone particles have a tendency to quickly or prematurely separate or to otherwise settle out from the slurry or paste such that application of a fairly homogeneous composition is rendered difficult or inconvenient, it can be advantageous to include within the composition a substance whose thixotropic characteristics prevent or reduce this tendency. Thus, e.g., where the wetting agent is water and/or glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, xanthan gum, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the wetting agent in an amount sufficient to significantly improve the suspension-keeping characteristics of the composition.

The binder is added in an amount to sufficiently provide a cohesive ground bone composite that can be used in skeletal repair and revisions methods without the ground bone coming apart. Preferably, the binder is present in an amount of from about 5% to about 80% w/v. More preferably, the binder may be present in a range of about 20% to about 66% w/v. More preferably, the binder may be present in an amount of from about 20 to about 50%. Another preferred range of binder is it being present in an amount of from about 15% to about 66% w/v.

Additionally, the particular binder used can be varied according to desired properties. For example, cyanoacrylates can be used as a binder in the production of cortical onlay plates and is preferably present in amount of from 20% to 30%. A binder may also be combined with at least one other binder. The binder is applied by injection, spray, bath, soaking or layering.

The above general ranges allow one of ordinary skill in the art to create a composite of proper density and mechanical properties and further allows the same basic device to be tailored to individual patients and situations.

As stated above, the preferred binder is a biocompatible cyanoacrylate. Preferred biocompatible cyanoacrylates include ester chain, N-butyl, and butyl cyanoacrylates. When a cyanoacrylate binder is used, a preferred amount is from about 5 to about 80%, preferably from about 20 to about 66%, more preferably from about 20 to about 50%. The cyanoacrylate binder may be combined with at least one other binder. More specifically, the cyanoacrylate binder described herein may also be a cyanoacrylate-comprising binder.

In addition to the materials described above, at least one other adhesive substance can optionally be used as a matrix to form composite bone material (in combination with or without at least one cyanoacrylate). For example, fibrin is a substance formed by human blood when it clots. Fibrin bonds the platelets together in the formation of, e.g., clots and scabs. Alternatively, fibrin glue can be manufactured. Other biocompatible adhesives can also be used. In addition, there exist a number of biocompatible gels which can be used as a matrix adhesive for holding bone powder together to form a composite.

The vacuum force applied to the mold typically ranges from about 29.9 inches of Hg to about 19.7 inches (based on a standard barometer reading of 29.92 inches of Hg at atmospheric pressure being 0% vacuum. Preferably, the vacuum force is about 29.5 inches Hg to about 24 inches Hg. Typically, the vacuum force is about 28 inches Hg.

Preferably, the vacuum force is applied simultaneous with the injection or spraying of binder. The vacuum force helps distribute the binder throughout the ground bone tissue.

The vacuum force is applied for a period of 1 second to about 10 minutes. Preferably, the vacuum force is applied for a period of less than about 1 minute. More preferably, the vacuum force is applied for a period of less than about 10 seconds.

In addition, pressure during formation can be tailored to the desired outcome. The pressure used in embodiments of the present invention can range from 14.7 psi to less than 1,000 psi. Lower pressures (i.e., from atmospheric to about 100 psi) can be used to form bone composites useful for skeletal repair and revision. Higher pressures (i.e., from about 100 psi to less than 1,000 psi) can be used to form bone composites useful for applications such as a bone screw, and typical load-bearing composites. Preferably, the compressive force is less than about 200 psi.

In certain embodiments of the present invention, a compressive force can be applied to the composite for a period of about 1 second to about 10 minutes. Also, preferably the compressive force application period overlaps (in whole or in part) with a vacuum application. That is, the compressive force may begin before a vacuum step is complete. Preferably, the compressive force is applied for a period of less than about one minute.

Following the application of the vacuum (and optional compressive force), the composite may be removed from the mold after a period in which the binder is outgassed. Typically the period is about 30 minutes.

Following removal from the mold, the composite may be shaped into the desired product. Alternatively, if the mold is shaped as the desired product, the composite may be inspected for any out of tolerance measurement or shape. Differences can be corrected in any number of ways, including with a light file, grinding, or milling. The composite can be sterilized and packaged.

As stated above, the process of the present invention comprises (i) providing bone tissue; (ii) grinding said bone tissue to form ground bone tissue; (iii) transferring said ground bone tissue into a mold; (iv) applying a binder to the bone tissue; (v) applying a vacuum to the mold; and (vi) optionally milling or refining the bone composite to the desired shape. In certain embodiments, the process of the present invention may comprise beginning the binder application at the same time the vacuum application begins. In another embodiment, the binder application may overlap in time (in whole or in part) with the vacuum period. Furthermore, a vacuum period may overlap in time (in whole or in part) with a compression period. Without being bound by theory, pressure and vacuum being applied at the same time helps assure even distribution of bone and binder.

In other embodiments, there may be a second vacuum period.

In a preferred embodiment, the process comprises the following steps: the ground bone tissue is placed in a mold, the vacuum pump is activated as the binder is injected, the pump is deactivated, compression begins, compression ends, a second vacuum period occurs, and the composite is removed from the mold.

Usually, it is desirable to allow the binder (especially a cyanoacrylate binder) to gas-off for a period of about 30 minutes after the molding process. Also, during this period, the wetting agent or hydrate can be allowed to evaporate. To accelerate gas-off and evaporation, the molded composite can be exposed to vacuum.

Furthermore, crosslinking, as described in U.S. Pat. No. 6,294,187 may be performed in order to improve the strength of the osteoimplant. Such crosslinking of the bone particle-containing composition can be effected by a variety of known methods including chemical reaction, the application of energy such as radiant energy, which includes irradiation by UV light or microwave energy, drying and/or heating and dye-mediated photo-oxidation; dehydrothermal treatment in which water is slowly removed while the bone particles are subjected to a vacuum; and, enzymatic treatment to form chemical linkages at any collagen-collagen interface. The preferred method of forming chemical linkages is by chemical reaction.

Chemical crosslinking agents include those that contain bifunctional or multifunctional reactive groups, and which react with surface-exposed collagen of adjacent bone particles within the bone particle-containing composition. By reacting with multiple functional groups on the same or different collagen molecules, the chemical crosslinking agent increases the mechanical strength of the osteoimplant.

Chemical crosslinking involves exposing the bone particles presenting surface-exposed collagen to the chemical crosslinking agent, either by contacting bone particles with a solution of the chemical crosslinking agent, or by exposing bone particles to the vapors of the chemical crosslinking agent under conditions appropriate for the particular type of crosslinking reaction. For example, the osteoimplant of this invention can be immersed in a solution of cross-linking agent for a period of time sufficient to allow complete penetration of the solution into the osteoimplant. Crosslinking conditions include an appropriate pH and temperature, and times ranging from minutes to days, depending upon the level of crosslinking desired, and the activity of the chemical crosslinking agent. The resulting osteoimplant is then washed to remove all leachable traces of the chemical.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; sugars, including glucose, will also crosslink collagen.

Glutaraldehyde crosslinked biomaterials have a tendency to over-calcify in the body. In this situation, should it be deemed necessary, calcification-controlling agents can be used with aldehyde crosslinking agents. These calcification-controlling agents include dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

When enzymatic treatment is employed, useful enzymes include those known in the art which are capable of catalyzing crosslinking reactions on proteins or peptides, preferably collagen molecules, e.g., transglutaminase as described in Jurgensen et al., The Journal of Bone and Joint Surgery, 79-a (2), 185–193 (1997).

Formation of chemical linkages can also be accomplished by the application of energy. One way to form chemical linkages by application of energy is to use methods known to form highly reactive oxygen ions generated from atmospheric gas, which in turn, promote oxygen crosslinks between surface-exposed collagen. Such methods include using energy in the form of ultraviolet light, microwave energy and the like. Another method utilizing the application of energy is a process known as dye-mediated photo-oxidation in which a chemical dye under the action of visible light is used to crosslink surface-exposed collagen.

Another method for the formation of chemical linkages is by dehydrothermal treatment which uses combined heat and the slow removal of water, preferably under vacuum, to achieve crosslinking of bone particles. The process involves chemically combining a hydroxy group from a functional group of one collagen molecule and a hydrogen ion from a functional group of another collagen molecule reacting to form water which is then removed resulting in the formation of a bond between the collagen molecules.

A preferred embodiment of the present invention is a method of forming a bone composite, comprising (i) providing bone tissue; (ii) grinding said bone tissue to form ground bone tissue ranging in size from about 125 microns to about 850 microns; (iii) transferring said ground bone tissue into a mold; (iv) applying a cyanoacrylate binder to the bone tissue; (v) applying a vacuum to the mold; (vi) applying a compressive force of less than 1000 psi to the mold; and (vii) optionally milling or refining the bone composite to the desired shape.

In this embodiment, the bone tissue is preferably substantially cortical bone tissue, and may be substantially demineralized. Most preferably, the bone tissue is greater than about 90% cortical bone tissue. Furthermore, a preferred vacuum force is about 20 Hg to about 25 Hg, and a preferred time is about 1 second to about 1 minute. The preferred compressive force occurs for a period of about 1 second to about 10 minutes and/or is less than 200 psi.

In this embodiment, (v) and (vi) may overlap in time; (iv) and (v) may overlap in time; (v) may be complete before (vi) is complete; and the method may comprise a second application of a vacuum after (vi) is complete.

Another embodiment of the present invention is a composite produces from any of the processes of the present invention.

Therefore, one embodiment of the present invention is an osteoinductive bone tissue composite that comprises ground bone tissue molded to form a desired shape; and a cyanoacrylate binder. Furthermore, the composite comprises random "voids". The voids are spaces between adjacent bone particles, and are present both at the surface of a composite as well as within the interior of the composite. These voids or spaces vary in size and shape and have a width of up to about 1,000 microns. Preferably the width of the void is from about 50–700 microns, more preferably from about 200–500 microns.

Preferably, the voids are present from about 5% to 50% (by volume of the composite). More preferably, the voids are present from about 15% to 35% (by volume), and more preferably, the voids are present in an about of about 25% (by volume).

The voids appear on the surface area of the composite as well. The presence of the voids on the surface area aids osteoconductivity. Thus, the composite of the present invention can be said as having an osteocinductive surface. A comparison of observations of a cut surface of a composite of the present invention and a cast surface of the present invention would show similar characteristics with respect to the voids.

The voids exist as a result of the process of the present invention, and their existence promote osteoconductivity of the composite. Without being bound by theory, the voids promote osteoconductivity because an influx of undifferentiated mesenchymal cells normally found within osseous structures as well as undifferentiated cells that migrate to the repair site to fill the voids. The action of the osteoinductive properties of the composite induce the undifferentiated cells to differentiate into bone-forming cells that both form bone within the voids as well as remodel the bone particles of the composite matrix into living host bone.

Many voids are interconnected one to the other, forming canals, channels, or tunnels that run throughout the composite. These canals are similar to haversian canals found in natural bone. The canals vary in size in shape, but typically have a width of about 10 to 500 microns, preferably from 100 to 200 microns.

The canals and voids work together to give the composite a preferred histo-anatomical structure that is similar to natural bone.

Figure 2:
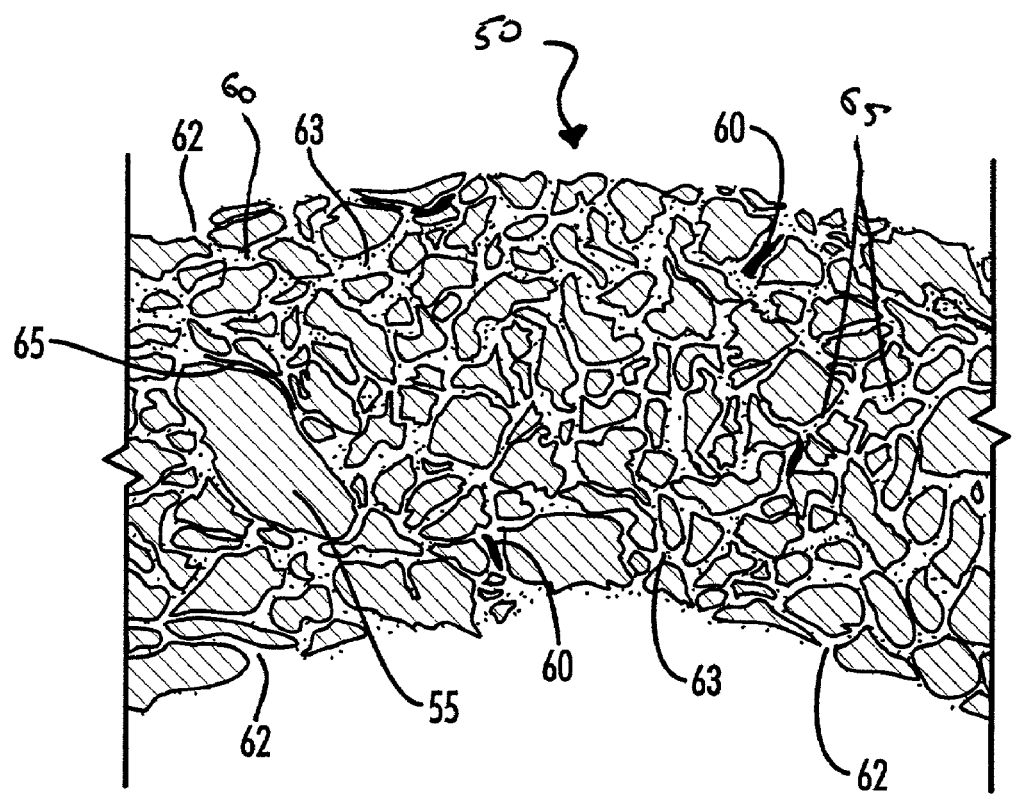
FIG. 2 shows a cross section drawing of an example of a bone composite of the present invention.
Figure 3:
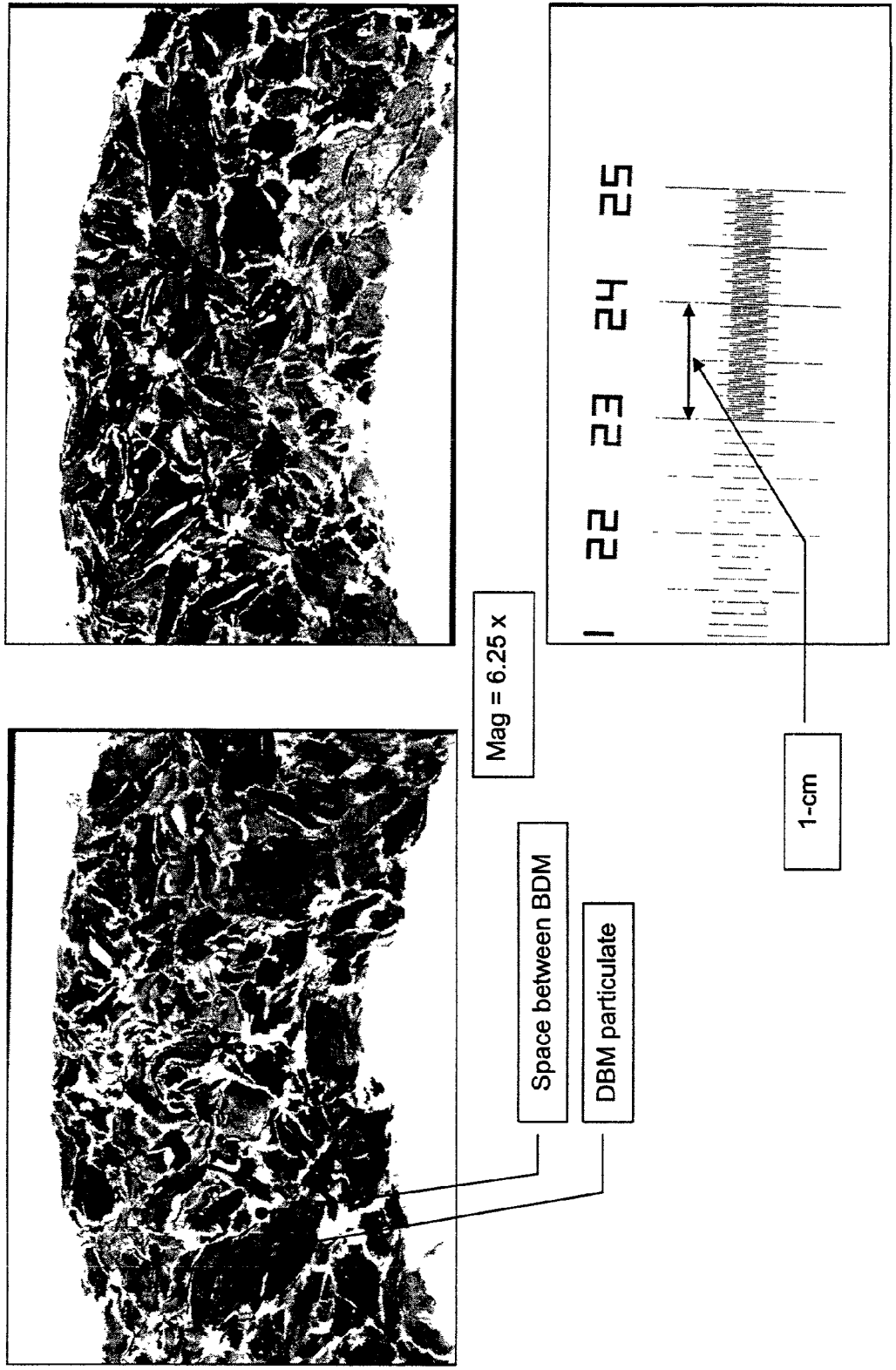
FIGS. 3 and 4 show magnified photographs of examples of a bone composite of the present invention.
Figure 4:
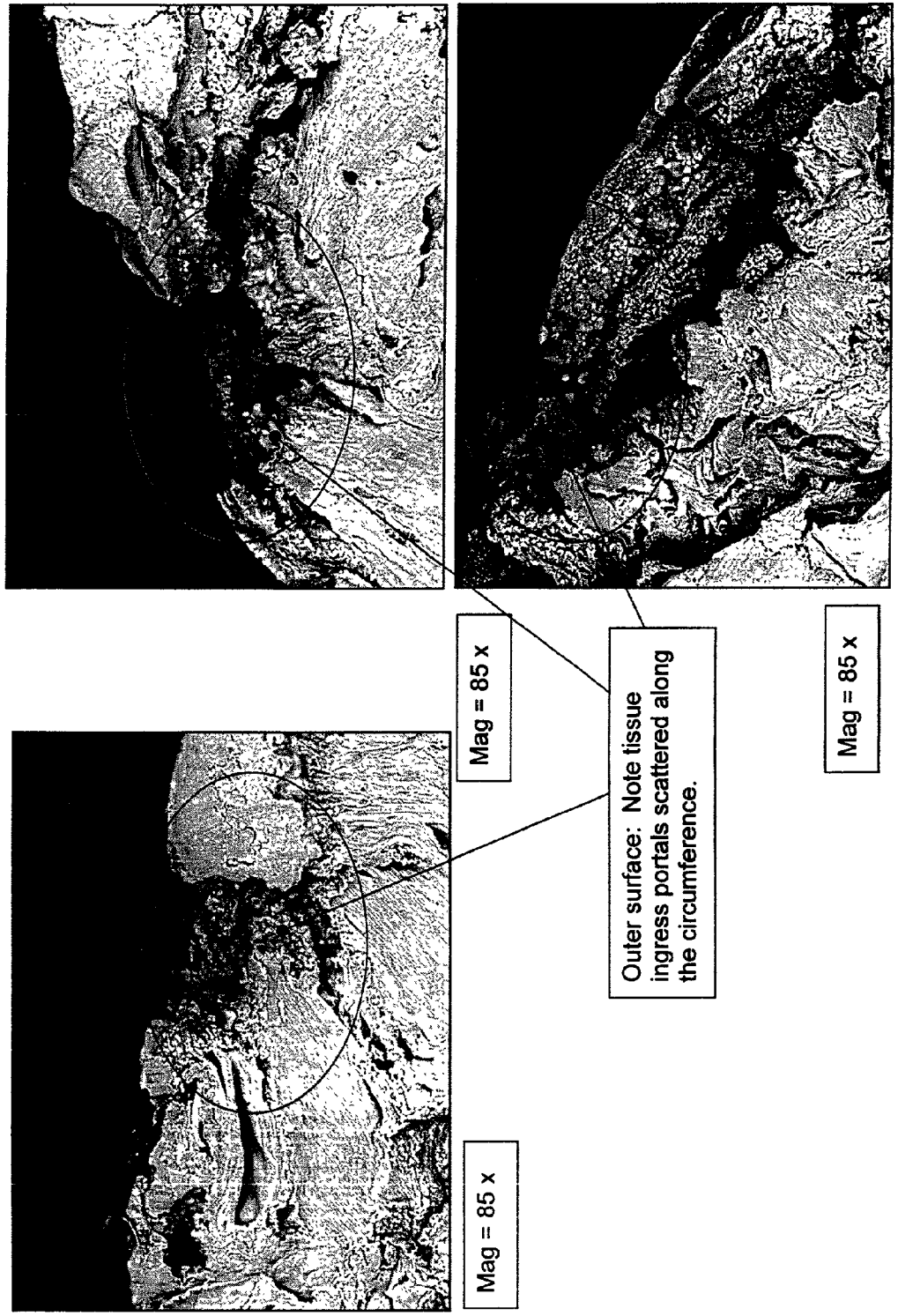

Now turning to the remaining drawings, FIG. 2 is a cross-section of an embodiment of a composite 50 of the present invention. The bone particles 55 are bordered in places by voids 60. The voids 60 join to form canals 65. Also shown in FIG. 2 are surface voids 62. FIG. 3 is a magnified (6.25×) photograph of a composite of the present invention. FIG. 4 is a magnified (85×) photograph of a composite of the present invention. The voids, canals, and bone particles described herein are visible.

As stated above, the composite of the present invention may be formed into a bone pin, screw, sheet, plate, disk, cylinder or prosthesis. In many i applications, the general shape can be formed in a specially-shaped mold, and then fine-tuned my milling, etc. after the molding process is complete. One of ordinary skill in the art would recognize many other beneficial uses for the composite of the present invention.

Of course, one of ordinary skill in the art would further recognize that the composite of the present invention may be molded and then later machined, milled, refined, or shaped by any suitable mechanical shaping means. Computerized modeling can, for example, be employed to provide an intricately-shaped composite which is custom-fitted to the bone repair site with great precision.

The following examples are intended to be for illustrative purposes and do not limit the spirit and scope of the present invention.

EXAMPLE 1

This example shows a process of making a tubular or cylindrical composite with a 2 cm OD (outside diameter) and 1.4 cm ID (inside diameter) by 2 cm in length, and 3 mm wall.

Cortical human bone is cleaned and ground into particles varying in size from 125 microns to 850 microns. The ground bone is demineralized, providing deminieralized bone matrix (DBM).

2.00 gms is measured, then hydrated with sterile water to a weight of 2.558 gms ($0.558H_2O$). The weighed DBM is then inserted into the cylindrical cavity of a Teflon® mold and manually compacted with a force of 0.5 pounds. One (1) cc of special blended N Butyl Cyanoacrylate (CA) is then injected with a #18 gauge needle into the DBM at the outer edge of the cylindrical shape, and at the same time a vacuum of 28" hg is applied from the bottom end of mold. Two (2) cc of same N Butyl Cyanoacrylate is then injected with a #18 gauge needle into the center core of the Teflon mold. The total weight of the bone composite is now 3.361 gms. This second injection occurs during application with the vacuum force. After the second injection, a maintained pneumatic force of 100 pounds is applied to the DBM with a maintained pneumatically generated vacuum of 28" Hg for 10 seconds.

Finally, the mold with the DBM composite is allowed to rest for a period of 30 minutes. When the 30-minute mold rest time is complete. Mold is manually dismantled and DBM bone composite is removed, placed on a Teflon mandrel that matches the I.D. of the tubular shaped DBM bone composite. Then allowed to gas-off for 30 minutes. Weight of composite is now 2.945 grams. The tubular shaped DBM bone composite is trimmed with a sharp instrument while still on mandrel, assuring proper outside dimensions. Mandrel assures inside dimensions and maintains inside dimensions as composite tries to contract. The tubular composite is found to be of good quality with even bonding throughout, may now be clean packaged and sterilized later.

EXAMPLE 2

Example 1 was repeated, to obtain the samples discussed below.

The densities of the samples were measured using physical density estimates and the water displacement method. Physical estimates measures a volume based upon physical measurement of the sample dimensions (height×width) and the dry weight of the sample. In this example, the samples were prepared by drying the sample in an oven at 110 C overnight. In the Water displacement method (ASTM D-792) the volume of water displaced is measured and the weight of the sample after drying is measured.

Density estimates based upon these two methods for five ART samples is presented in Table 1.

TABLE 1

| | Measured Density | | |
|---|---|---|---|
| Sample ID | Water Displacement density estimate, gms/cc | | Physical Density Estimate, gms/cc |
| Human-1-A | 1.12 | 1.12 | 1.00 |
| Human-1-B | 0.96 | 0.98 | 0.86 |
| Rabbit-3 | 0.96 | 1.07 | 0.96 |
| Rabbit-4 | 1.09 | 1.07 | 0.83 |
| Rabbit-5 | 1.07 | 1.07 | 0.91 |
| Mean | 1.04 | 1.062 | 0.912 |
| | | 1.051 | |

The weight loss on drying is presented in Table 2. The weight loss on drying is a combination of water losses from evaporation of the water trapped within the spaces within the sample as well as the water contained within the DBM material.

TABLE 2

| Sample ID | Wet weight, gms | Dry Weight, gms | Weight loss on drying, gms | Percent weight loss on drying |
|---|---|---|---|---|
| Human-1-A | 1.1235 | 0.7568 | 0.3667 | 32.64% |
| Human-1-B | 1.2309 | 0.7932 | 0.4377 | 35.56% |
| Rabbit-3 | 1.2999 | 0.8184 | 0.4815 | 37.04% |
| Rabbit-4 | 1.152 | 0.6846 | 0.4674 | 40.57% |
| Rabbit-5 | 1.1853 | 0.7489 | 0.4364 | 36.82% |
| Mean | 1.19832 | 0.76038 | 0.43794 | 36.53% |

All patents, journal articles, and other publications cited in this disclosure are hereby expressly incorporated by reference.

From the foregoing description of the present invention, those skilled in the art will perceive improvements, changes and modifications, and understand that the specific details shown herein are merely illustrative. Such changes, modifications, and improvements do not depart from the spirit and scope of the following claims.

I claim:

1. A method of forming a bone composite, comprising:
   (i) providing bone tissue;
   (ii) grinding said bone tissue to form ground bone tissue;
   (iii) transferring said ground bone tissue into a mold and compacting said ground bone tissue while maintaining canals within said around bone tissue to form a bone composite;
   (iv) applying a binder to the bone tissue to set within said ground bone tissue and to partially fill the canals of said around bone tissue;
   (v) applying a vacuum to the mold concurrently with step (iv) to substantially evenly disperse the binder throughout said ground bone tissue; and
   (vi) optionally milling or refining the bone composite to the desired shape.

2. The method of claim 1, wherein the binder is present in an amount of from about 5% to about 80% (w/v).

3. The method of claim 1, wherein the binder is present in an amount of from about 20% to about 50% (w/v).

4. The method of claim 1, wherein the ground bone tissue is greater than 90% cortical bone tissue.

5. The method of claim 1, wherein the ground bone tissue is greater than 95% cortical bone tissue.

6. The method of claim 1, wherein the ground bone tissue is from 125 to 850 microns in size.

7. The method of claim 1, wherein the binder is applied by an injection, spray, bath, soaking or layering.

8. The method of claim 1, wherein the binder is a biological adhesive, bioactive glass ceramic, dental resin sealant, glass ionomer cement, gelatin-resorcinol-formaldehyde glue, collagen-based glue, cellulosic, bioabsorbable polymer, nonbioabsorbable polymer, starch ethylenevinyl alcohol, polycyanoacrylate, or polyphosphazene.

9. The method of claim 1, wherein the bone composite is a bone pin, screw, sheet, plate, disk, cylinder or prosthesis.

10. The method of claim 1, which further comprises applying a filler, fiber, plasticizer, biostatic/biocidal agent, surface active agent, or bioactive agent to the bone tissue.

11. The method of claim 1, wherein the vacuum force is about 29.9 inches Hg to about 19.7 inches Hg.

12. The method of claim 1, wherein the vacuum force is about 29.5 inches Hg to about 24 inches Hg.

13. The method of claim 1, wherein the vacuum is applied to the mold for a period of about 1 second to about 10 minutes.

14. The method of claim 1, wherein the vacuum is applied to the mold for a period of about 1 second to less than about 1 minute.

15. The method of claim 1, wherein the compressive force is applied for a period of 1 second to about 10 minutes.

16. The method of claim 1, wherein the (iv) begins at the same time as (v).

17. The method of claim 1, wherein (iv) and (v) overlaps in time.

18. The method of claim 1, wherein (v) overlaps in time with the application of a compressive force of less than 1,000 psi to the mold.

19. The method of claim 1, further comprising: applying a compressive force of less than 1000 psi to the mold to compact said ground bone tissue.

20. The method of claim 19, wherein the compressive force is less than 200 psi.

21. The method of claim 19, wherein the compressive force is applied before (v) is complete.

22. The method of claim 1, wherein the bone tissue is substantially cortical bone tissue.

23. The method of claim 22, wherein the bone tissue is substantially demineralized.

24. The method of claim 22, wherein the bone tissue is greater than 70% cortical bone tissue.

25. The method of claim 1, wherein the binder comprises cyanoacrylates.

26. The method of claim 25, wherein the cyanoacrylates comprise ester chain, N-butyl, or butyl cyanoacrylates.

27. The method of claim 25, wherein the cyanoacrylates are long chain cyanoacrylates.

28. The method of claim 1, wherein the ground bone tissue is hydrated after the grinding step.

29. The method of claim 28, wherein the ground bone tissue is hydrated in an amount of 1 to about 5% (volume).

30. The method of claim 28, wherein the hydrate is demineralized water.

31. A method of forming a bone composite, comprising:
   (i) providing bone tissue;
   (ii) grinding said bone tissue to form ground bone tissue ranging in size from about 125 microns to about 850 microns;.
   (iii) hydrating and transferring said ground bone tissue into a mold and compacting said ground bone tissue while maintaining voids within said around bone tissue to form a bone composite;
   (iv) applying a cyanoacrylate binder to the bone tissue to set within said ground bone tissue and to partially fill the voids of said around bone tissue;
   (v) applying a vacuum to the mold concurrently with step (iv) to substantially evenly disperse the cyanoacrylate binder throughout said ground bone tissue;
   (vi) applying a compressive force of less than 1000 psi to the mold to compact said ground bone tissue; and
   (vii) optionally milling or refining the bone composite to the desired shape.

32. The method of claim 31, wherein the bone tissue is substantially cortical bone tissue.

33. The method of claim 31, wherein the bone tissue is substantially demineralized.

34. The method of claim 31, wherein the bone tissue is greater than about 90% cortical bone tissue.

35. The method of claim 31, wherein the vacuum force is about 29.5 inches Hg to about 24 inches Hg.

36. The method of claim 31, wherein the vacuum time is about 1 second to about 1 minute.

37. The method of claim 31, wherein the compressive force occurs for a period of about 1 second to about 10 minutes.

38. The method of claim 31, wherein (v) and (vi) overlap in time.

39. The method of claim 31, wherein (iv) and (v) overlap in time.

40. The method of claim 31, wherein the compressive force is less than 200 psi.

41. The method of claim 31, wherein (v) is complete before (vi) is complete.

42. The method of claim 41, further comprising a second application of a vacuum after (vi) is complete.

* * * * *